US010385151B2

(12) United States Patent
Fukagawa

(10) Patent No.: US 10,385,151 B2
(45) Date of Patent: Aug. 20, 2019

(54) MATERIAL NON-ADHESIVE TO BIOLOGICAL SUBSTANCE, CURABLE COMPOSITION, AND ARTIFICIAL ORGAN AND MEDICAL INSTRUMENT USING SAME

(71) Applicant: FUJIFILM Corporation, Tokyo (JP)

(72) Inventor: Kiyotaka Fukagawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/581,703

(22) Filed: Apr. 28, 2017

(65) Prior Publication Data
US 2017/0226251 A1    Aug. 10, 2017

Related U.S. Application Data

(63) Continuation of application No. PCT/JP2015/077131, filed on Sep. 25, 2015.

(30) Foreign Application Priority Data

Oct. 29, 2014  (JP) ................................ 2014-220307
Feb. 5, 2015  (JP) ................................ 2015-021539
Jul. 29, 2015  (JP) ................................ 2015-149458

(51) Int. Cl.
*C08F 220/60*    (2006.01)
*C08F 228/02*    (2006.01)
(Continued)

(52) U.S. Cl.
CPC ............ *C08F 220/60* (2013.01); *A61L 27/00* (2013.01); *A61L 27/34* (2013.01); *A61L 29/00* (2013.01);
(Continued)

(58) Field of Classification Search
CPC .......... C08F 2220/606; C08F 2220/603; C08F 228/02; C08F 220/60; A61L 27/34
See application file for complete search history.

(56) References Cited

U.S. PATENT DOCUMENTS 6,497,868 B1    12/2002  Tanahashi
2008/0181861 A1*  7/2008  Jiang ..................... B82Y 30/00
                                                        424/78.09
(Continued)

FOREIGN PATENT DOCUMENTS

CN    103880714 A    6/2014
EP    1892080 A1    2/2008
(Continued)

OTHER PUBLICATIONS

Kazuyuki Ishihara, et al., "Sosei Ion-ki o Yusuru Kobunshi no Seitai Tekigosei ni Kansuru Kenkyu", The 58th Polymer Preprints, Japan, 2009, 1PB138, session ID:3M-07.
(Continued)

*Primary Examiner* — Ling Siu Choi
*Assistant Examiner* — David L Miller
(74) *Attorney, Agent, or Firm* — Sughrue Mion, PLLC

(57) ABSTRACT

A material non-adhesive to a biological substance containing: a polymer compound (A) which includes a repeating unit derived from a sulfobetaine monomer represented by Formula (I) or (II).

(Continued)

Glass    Coated

-continued

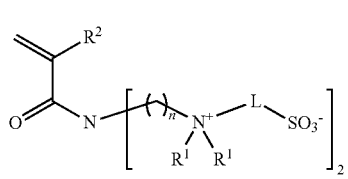

(II)

In the formulae, $R^1$ represents a methyl group, an ethyl group, an n-propyl group, or an isopropyl group, a plurality of $R^1$'s may be the same as or different from each other.

$R^2$ represents a hydrogen atom or a methyl group.

n represents an integer of 2 to 4.

L represents a linear or branched alkylene group having 3 or 4 carbon atoms.

9 Claims, 1 Drawing Sheet

(51) Int. Cl.
 *A61L 27/00*  (2006.01)
 *A61L 29/00*  (2006.01)
 *A61L 31/00*  (2006.01)
 *A61L 33/00*  (2006.01)
 *C08F 20/60*  (2006.01)
 *A61L 27/34*  (2006.01)
 *A61L 31/10*  (2006.01)
 *C08F 220/18*  (2006.01)
 *C08F 220/28*  (2006.01)

(52) U.S. Cl.
CPC ............... *A61L 31/00* (2013.01); *A61L 31/10* (2013.01); *A61L 33/00* (2013.01); *C08F 20/60* (2013.01); *C08F 220/18* (2013.01); *C08F 220/28* (2013.01); *C08F 228/02* (2013.01); *C08F 2220/1825* (2013.01); *C08F 2220/603* (2013.01); *C08F 2220/606* (2013.01)

(56) References Cited

U.S. PATENT DOCUMENTS

2008/0262181 A1 10/2008 Kitano et al.
2010/0004152 A1* 1/2010 Karagianni ......... C08F 293/005
                 510/180
2014/0100390 A1 4/2014 Amao et al.

FOREIGN PATENT DOCUMENTS

| JP | 07-227917 A | | 8/1995 |
|---|---|---|---|
| JP | 07-300513 A | | 11/1995 |
| JP | 07300513 A | * | 11/1995 |
| JP | 10-081717 A | | 3/1998 |
| JP | 2007-516794 A | | 6/2007 |
| JP | 2009-508542 A | | 3/2009 |
| JP | 4719146 B2 | | 7/2011 |
| JP | 2011-173867 A | | 9/2011 |
| WO | 2005/113620 A1 | | 12/2005 |
| WO | 2007/024393 A2 | | 3/2007 |
| WO | 2012/133182 A1 | | 10/2012 |

OTHER PUBLICATIONS

Sho Saito, et al., "Sulfobetaine Polymer no Denka-kan Kyori to Seitai Tekigosei tono Sokan", The 60th Polymer Preprints, Japan, 2011, 1PE127.

Hiromi Kitano, et al., "Correlation between Biocompatibility of Polymer Materials and Their Hydration Structure", Kobunshi, 2009, pp. 74-77, vol. 58, No. 2.

International Search Report for PCT/JP2015/077131 dated Oct. 27, 2015 [PCT/ISA/210].

Communication dated Oct. 26, 2017 issued by the European Patent Office in counterpart application No. 15855694.4.

Joseph B. Schlenoff: "Zwitteration: Coating Surfaces with Zwitterionic Functionality to Reduce Nonspecific Adsorption", Langmuir, vol. 30, No. 32, Aug. 19, 2014 (Aug. 19, 2014), pp. 9625-9636, XP55406750 (12 pages total).

Mei-Chan Sin et al: "Hemocompatibility of zwitterionic interfaces and membranes", Polymer Journal., vol. 46, No. 8, Jun. 18, 2014 (Jun. 18, 2014), pp. 436-443, XP55406753 (8 pages total).

Pingsheng Liu et al.: "Sulfobetaine as a zwitterionic mediator for 3D hydroxyapatite mineralization", Biomaterials., vol. 34, No. 10, Jan. 16, 2013 (Jan. 16, 2013), pp. 2442-2454, XP055234563 (13 pages total).

Louisa R. Carr et al: "Functionalizable and nonfouling zwitterionic carboxybetaine hydrogels with a carboxybetaine dimethacrylate crosslinker", Biomaterials, Elsevier Science Publishers BV., Barking, BG, vol. 32, No. 4, Feb. 1, 2011 (Feb. 1, 2011), pp. 961-968, XP027514824 (8 pages total).

Communication dated Jan. 30, 2018 from the Japanese Patent Office in counterpart Application No. 2016-556439.

Translation of International Preliminary on Patentability dated Oct. 27, 2015 in counterpart International Application No. PCT/JP2015/077131.

Communication dated Oct. 8, 2018 from European Patent Office in counterpart Application No. 15 855 694.4.

* cited by examiner

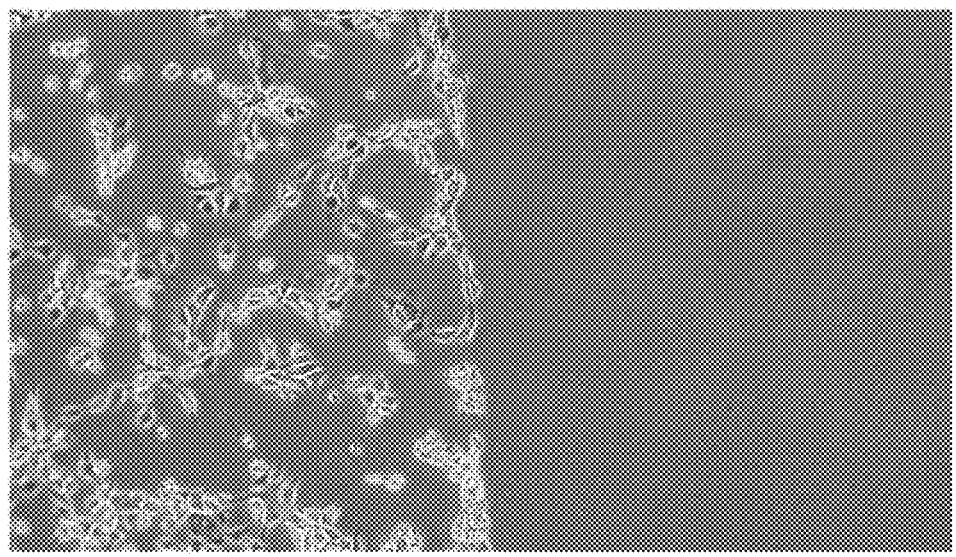

MATERIAL NON-ADHESIVE TO BIOLOGICAL SUBSTANCE, CURABLE COMPOSITION, AND ARTIFICIAL ORGAN AND MEDICAL INSTRUMENT USING SAME

CROSS-REFERENCE TO RELATED APPLICATIONS

This application is a Continuation of PCT International Application No. PCT/JP2015/077131 filed on Sep. 25, 2015, which claims priority under 35 U.S.C. § 119 (a) to Japanese Patent Application No. 2014-220307 filed on Oct. 29, 2014, to Japanese Patent Application No. 2015-021539 filed on Feb. 5, 2015, and to Japanese Patent Application No. 2015-149458 filed on Jul. 29, 2015. Each of the above applications is hereby expressly incorporated by reference, in its entirety, into the present application.

BACKGROUND OF THE INVENTION

1. Field of the Invention

The present invention relates to a material non-adhesive to a biological substance, a curable composition, and an artificial organ and a medical instrument using the same.

2. Description of the Related Art

It is desired that artificial internal organs or medical instruments are prepared using materials which are compatible with a substance constituting an original organism and are unlikely to be fouled. For example, it is desired that artificial blood vessels, catheters, stents, artificial bones, and the like, which are introduced to a human body for a long term, do not cause an inflammatory reaction or a rejection reaction. Further, when these artificial organs or medical instruments are replaced due to fouling, this results in a burden of a patient. The same applies to medical instruments such as a blood preservation pack and a hemodialysis membrane and these medical instruments need to be frequently replaced if these medical instruments are easily fouled due to adhesion of cells or blood.

Various materials are used for artificial organs such as artificial internal organs and artificial bones or medical instruments according to the required characteristics. Silicone materials are selected in consideration of flexibility and inorganic materials such as glass or metal are selected in consideration of durability. Alternatively, various resin materials are occasionally applied at the time of focusing on productivity or cost.

JP4719146B discloses a biocompatible material which includes a polymer of a specific amino acid type betaine monomer and a specific polymerizable monomer. With this, it is possible to provide a material with excellent biocompatibility, for example, having small interaction with biological components such as protein or blood corpuscles.

SUMMARY OF THE INVENTION

The present invention focuses on non-adhesive properties to a biological substance required for the above-described artificial organs or medical instruments. It is expected that the artificial organs or medical instruments can be used longer than the related art by making the biological substance difficult to adhere to such members or instruments. In this manner, it becomes possible to hygienically use medical instruments or the like. From this viewpoint, a technique for realizing the non-adhesive properties to a biological substance becomes useful in various fields without limitation to artificial organs or medical instruments.

An object of the present invention is to provide a material non-adhesive to a biological substance which is capable of suppressing or preventing adhesion of a biological substance such as a cell or a blood component; a curable composition which is used as a raw material thereof; and an artificial organ and a medical instrument using the same.

According to the present invention, the above-described problems are solved by the following means.

[1] A material non-adhesive to a biological substance containing: a polymer compound (A) which includes a repeating unit derived from a sulfobetaine monomer represented by Formula (I) or (II),

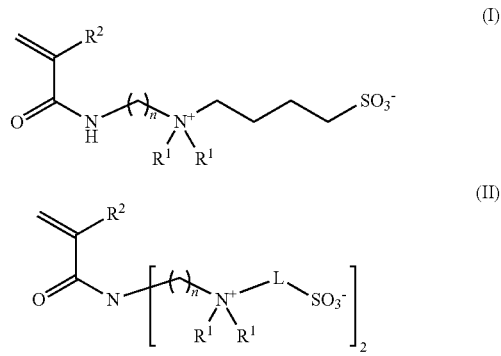

in the formulae, $R^1$ represents a methyl group, an ethyl group, an n-propyl group, or an isopropyl group, and a plurality of $R^1$'s may be the same as or different from each other, $R^2$ represents a hydrogen atom or a methyl group, n represents an integer of 2 to 4, and L represents a linear or branched alkylene group having 3 or 4 carbon atoms.

[2] The material non-adhesive to a biological substance according to [1], in which the monomer represented by Formula (I) is a monomer represented by the following Formula (I-1).

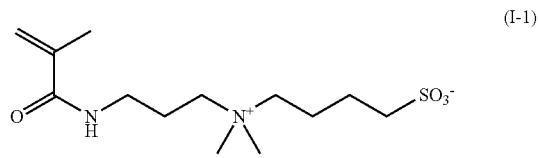

[3] The material non-adhesive to a biological substance according to [1], in which the monomer represented by Formula (II) is a monomer represented by the following Formula (II-1).

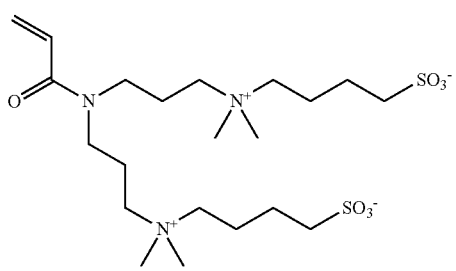

(II-1)

[4] The material non-adhesive to a biological substance according to any one of [1] to [3], in which the polymer compound (A) includes a repeating unit derived from a monomer having an ethylenically unsaturated group.

[5] The material non-adhesive to a biological substance according to any one of [1] to [4], in which the content of the repeating unit derived from the sulfobetaine monomer in the polymer compound (A) is in a range of 5% to 90%, on a mass basis.

[6] The material non-adhesive to a biological substance according to any one of [1] to [5], in which the biological substance is a cell or protein.

[7] The material non-adhesive to a biological substance according to any one of [1] to [6], in which a C Log P value of the sulfobetaine monomer is −20 or greater and less than −7.2.

[8] The material non-adhesive to a biological substance according to any one of [1] to [7] which is used for a medical instrument or an artificial organ.

[9] The material non-adhesive to a biological substance according to any one of [1] to [8] which is a film or a resin composition used to form the film; or a structure or a resin composition used to form the structure.

[10] The material non-adhesive to a biological substance according to any one of [1] to [9] which is a liquid composition type material.

[11] The material non-adhesive to a biological substance according to any one of [1] to [9] which is a curable resin composition type material.

[12] An artificial organ comprising: the material non-adhesive to a biological substance according to any one of [1] to [11] in at least a portion thereof.

[13] A medical instrument comprising: the material non-adhesive to a biological substance according to any one of [1] to [11] in at least a portion thereof.

[14] A curable composition which is used to form a material non-adhesive to a biological substance, containing: a sulfobetaine monomer represented by Formula (I) or (II),

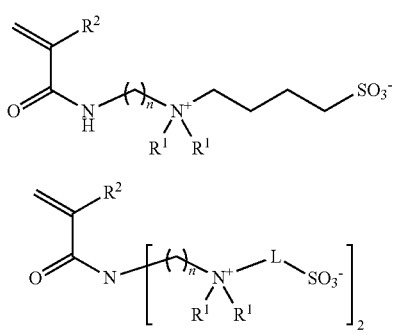

in the formulae, $R^1$ represents a methyl group, an ethyl group, an n-propyl group, or an isopropyl group, and a plurality of $R^1$'s may be the same as or different from each other, $R^2$ represents a hydrogen atom or a methyl group, n represents an integer of 2 to 4, and L represents a linear or branched alkylene group having 3 or 4 carbon atoms.

[15] The curable composition according to [14], further containing: a polymerization initiator.

[16] The curable composition according to [14] or [15], further containing: a monomer which includes an ethylenically unsaturated group.

In the present specification, the form of the "material non-adhesive to a biological substance" is not particularly limited. The material may be in the form of a liquid, powder, a film, or a structure. Examples thereof widely include a coating film or a coating liquid used to form the coating film, paste, a dispersion liquid, a film material or a dope used to form the film material, a formed product, a structure, and a resin composition used to form a formed product and a structure.

In the present specification, the meaning of the "biological substance" in the present specification includes a material constituting an organism or a material related to an organism in a broad sense. Examples thereof mean to include protein, cells, tissues formed by cells being collected, peptides, vitamins, hormones, blood corpuscles, antigens, antibodies, bacteria, and virus.

In the present specification, the "non-adhesive properties" means not only observing no adhesion but also observing suppressed adhesion (reduction in adhesion amount) before and after application even when adhesion is seen. Therefore, the concept of "non-adhesive properties" means to include not only prevention of adhesion but also suppression of adhesion.

According to the material non-adhesive to a biological substance of the present invention, it is possible to suppress or prevent adhesion of cells or blood components to a biological substance. Further, the material non-adhesive to a biological substance contributes to provision of not only artificial organs or medical instruments but also various sanitary products or members with improved biocompatibility, using the non-adhesive properties to the biological substance. The artificial organs or medical instruments of the present invention have excellent non-adhesive properties to a biological substance. Further, it is possible to suitably prepare a material non-adhesive to a biological substance having the above-described excellent characteristics using the curable composition of the present invention.

The above-described and other features and advantages of the present invention will become evident from the description below with reference to the accompanying drawings.

BRIEF DESCRIPTION OF THE DRAWINGS

FIG. 1 is a phase contrast microphotograph showing results of a cell adhesion test performed in Reference Example 1 and Comparative Example 1 (magnification: 4 times).

DESCRIPTION OF THE PREFERRED EMBODIMENTS

A material non-adhesive to a biological substance of the present invention contains a polymer compound (A) having a repeating unit derived from a monomer (hereinafter, also referred to as a specific sulfobetaine monomer) represented by Formula (I) or (II). In this manner, the reason why the above-described effects are obtained is unclear, but the mechanism for the action may be explained in the following manner. The repeating unit derived from a betaine monomer has a positively charged moiety and a negatively charged moiety. There are suitable regions in accordance with the type of polar group or applied applications for the distance or disposition thereof, and the region is considered to exhibit desired characteristics within a specific range. In addition, it is considered that a network is formed by an action of the above-described charged moiety of a betaine monomer.

Meanwhile, in the present invention, a sulfobetaine monomer having a specific structure is employed as a raw material of a polymer compound. In this manner, it is understood that characteristics of a moderate amphoteric moiety are exhibited and a preferable network can be formed through the moiety. Therefore, it is considered that a material which effectively exhibits non-adhesive properties to a biological substance and has high versatility suitable for various forms of use can be obtained. Hereinafter, preferred embodiments of the present invention will be described in detail.

[Specific Sulfobetaine Monomer]

A monomer represented by Formula (I) or (II) has the following structure.

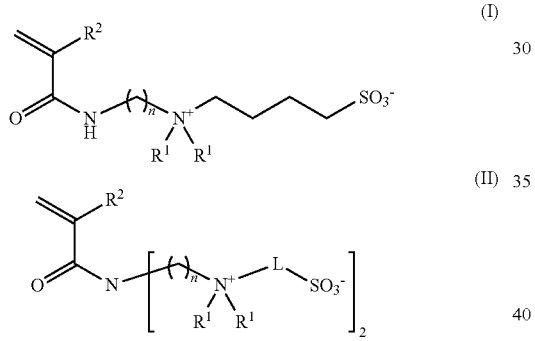

In the formulae, $R^1$ represents a methyl group, an ethyl group, an n-propyl group, or an isopropyl group. When a plurality of $R^1$'s are present in a molecule, the plurality of $R^1$'s may be the same as or different from each other. From the viewpoint of easily synthesizing a monomer, it is preferable that all $R^1$'s represent the same substituent. Among the examples of the substituent, it is particularly preferable that all $R^1$'s represent a methyl group. In addition, two structures in the parentheses in Formula (II) may be the same as or different from each other, but it is preferable that the two structures are the same as each other from the viewpoint of convenience of synthesization.

$R^2$ represents a hydrogen atom or a methyl group.

n represents an integer of 2 to 4. When n is large and the alkylene chain of this portion is extremely large, solubility in a solvent may be degraded. When the alkylene chain of this portion is extremely short, mobility of an ammonium cation moiety is decreased and adhesiveness to base materials (for example, various resin films such as PET, various plastics, various metals, or glass) used for coating may be affected. In a case where the adhesiveness is degraded, since the coating surface is peeled off, effects of non-adhesive properties to a biological substance may be poor in some cases. From this viewpoint, it is particularly preferable that n represents 3.

L represents a linear or branched alkylene group having 3 or 4 carbon atoms, and specific examples thereof include the following structures (the symbol "*" represents a binding site).

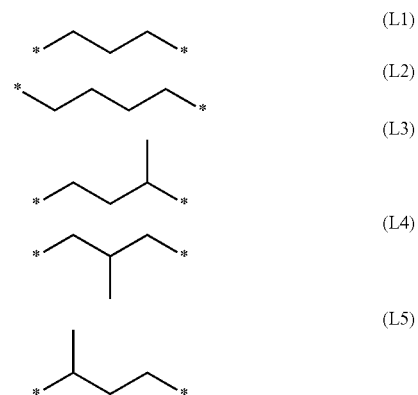

From the viewpoint of suitably exhibiting effects of the present invention, it is particularly preferable that L represents an n-butylene group (L2).

It is preferable that the monomer represented by Formula (I) is a monomer represented by the following Formula (I-1).

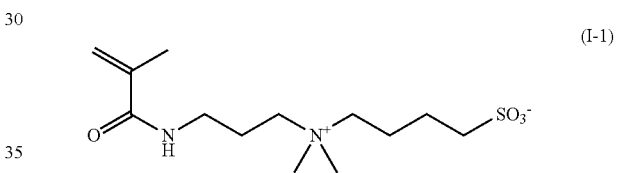

It is preferable that the monomer represented by Formula (II) is a monomer represented by the following Formula (II-1).

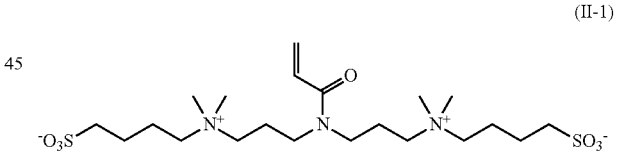

It is preferable that the C Log P value of the specific sulfobetaine monomer is set to be in a predetermined range. The C Log P value thereof is preferably less than −7.2, more preferably −7.5 or less, still more preferably −7.8 or less, even still more preferably −8 or less, even still more preferably −8.2 or less, even still more preferably −8.5 or less, even still more preferably −8.7 or less, and particularly preferably −9 or less. The lower limit thereof is practically −20 or greater. The C Log P value of the monomer represented by Formula (I) is preferably −12 or greater and more preferably −10 or greater. The C Log P value of the monomer represented by Formula (II) is preferably −20 or greater and more preferably −19 or greater. Since the non-adhesive properties to a biological substance can be improved by exhibiting excellent hydrophilicity, it is preferable that the upper limit of the C Log P value is set to be in the above-described range.

A "Log P value" is a coefficient indicating an affinity of an organic compound for water and 1-octanol. A 1-octanol/water partition coefficient P is a distribution equilibrium at the time of dissolving, as a solute, a trace amount of compound in a solvent of two liquid phases of 1-octanol and water, is a ratio between the equilibrium concentrations of a compound in each solvent, and is represented by a logarithm Log P of these with respect to a radix of 10. That is, the "Log P value is a logarithm value of a distribution coefficient of 1-octanol/water and is known as a parameter representing hydrophilicity of a molecule.

A "C Log P value" is a Log P value obtained by calculation. The C Log P value can be calculated according to a fragment method or an atomic approach method. More specifically, the fragment method described in the literature (C. Hansch & A. Leo, "Substituent Constants for Correlation Analysis in Chemistry and Biology" (John Wiley & Sons, New York, 1969)), commercially available software "Chem Bio Draw Ultra ver. 12.0 (Cambridgesoft Corporation, USA), or the like may be used to calculated the C Log P value. The numerical value of the CLog P value described in the specification of the present application is a "C Log P value" calculated using the above-described software (Chem Bio Draw Ultra ver. 12.0 (Cambridgesoft Corporation, USA)).

Specific examples of the sulfobetaine monomer and the C Log P value thereof will be described below. However, the present invention is not limitatively interpreted to these examples. In addition, compounds numbered with cex are comparative examples or reference examples.

| No. | Structure | CLogP |
|---|---|---|
| cex1 | 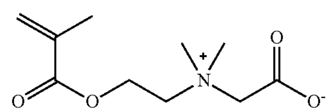 | −5.8 |
| cex2 | 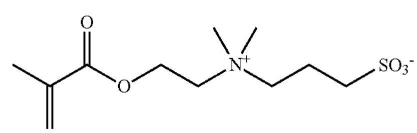 | −6.1 |
| cex3 | 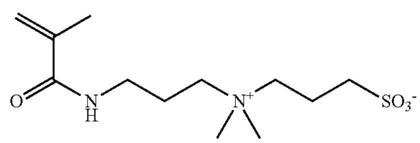 | −7.2 |
| ex1 | 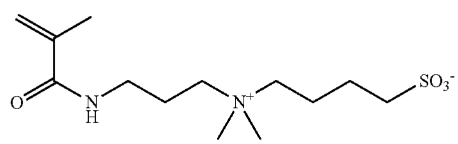 | −9.5 |
| ex2 | 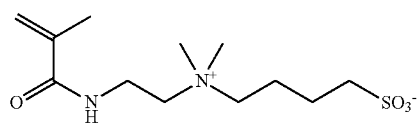 | −8.6 |
| ex3 | 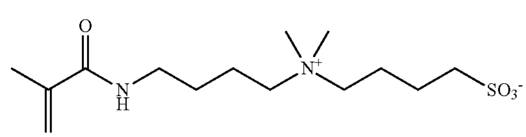 | −10.9 |
| ex4 | 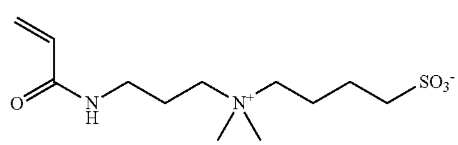 | −9.8 |
| ex5 | 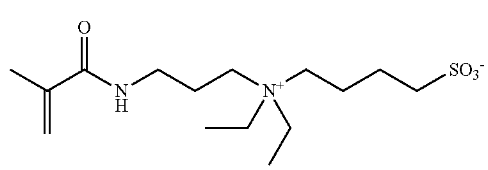 | −8.5 |

| No. | Structure | CLogP |
|---|---|---|
| ex6 | 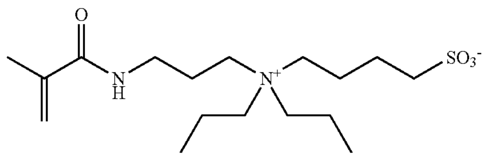 | −7.4 |
| ex7 | 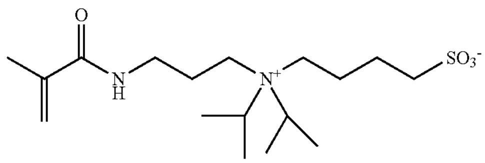 | −7.8 |
| ex8 | 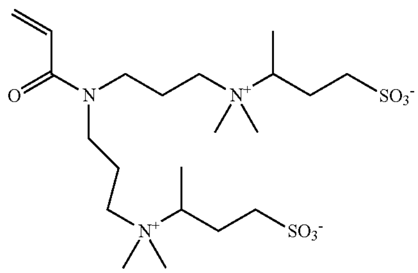 | −13.2 |
| ex9 | 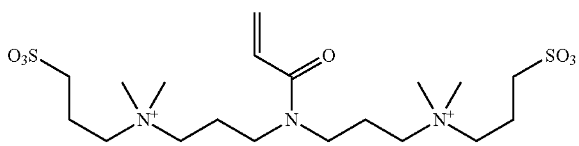 | −13.8 |
| ex10 | 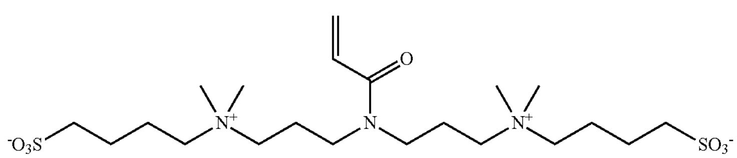 | −18.5 |

The above-described sulfobetaine monomer can be synthesized using a conventional method. For example, the synthesis examples or exemplary compounds disclosed in JP2012-187907A and JP2012-31400A can be referred to. Specifically, a (meth)acrylamide compound containing an amino group is obtained by reacting a predetermined polyamine compound with a (meth)acrylic acid chloride compound. A compound having a sulfobetaine structure can be obtained by reacting a sultone compound having a predetermined number of carbon atoms with the obtained (meth)acrylamide compound. Specifically, the description in paragraphs [0189] to [0193] of JP2012-31400A can be referred to.

In addition, the polymer compound (A) having a repeating unit derived from a sulfobetaine monomer represented by Formula (I) or (II) has the same definition as that for a polymer compound which is subjected to addition polymerization by a vinyl group thereof and has a repeating unit represented by the following Formula (Ia) or (IIa).

$R^1$, $R^2$, n, and L in the formulae have the same definitions as those for $R^1$, $R^2$, n, and L in Formulae (I) and (II).

[Copolymer Component]

The polymer compound (A) of the present invention may be a homopolymer of a specific sulfobetaine monomer or a copolymer with a copolymerizable monomer. A monomer (ethylenic monomer) having an ethylenically unsaturated group is exemplified as a copolymerizable monomer, and it is preferable that the polymer compound (A) has a repeating unit derived from a monomer having an ethylenically unsaturated group. Examples thereof include (meth)acrylic acid ester (acrylic acid ester or methacrylic acid ester) such as methyl (meth)acrylate, ethyl (meth)acrylate, n-butyl (meth)acrylate, 2-ethylhexyl (meth)acrylate, 2-hydroxyethyl (meth)acrylate, 2-hydroxypropyl (meth)acrylate, 3-(meth) acryloyloxypropylsulfonic acid, N,N,-dimethylaminoethyl (meth)acrylate, N,N-diethylaminoethyl (meth)acrylate, polyalkylene glycol mono(meth)acrylate, polyalkylene glycol di(meth)acrylate, or 2-(meth)acryloyloxy ethyl methyl sulfoxide. Further, other examples thereof include a carboxyl group-containing ethylenic monomer such as (meth) acrylic acid (acrylic acid, methacrylic acid), crotonic acid, or itaconic acid. In addition, various ethylenic monomers such as styrene, vinyl chloride, acrylonitrile, vinyl pyridine, vinyl pyrrolidone, and p-styrenesulfonic acid may be exemplified. Further, a (meth)acrylamide monomer such as (meth)acrylamide, (meth)acrylamido-2-methyl-propanesulfonic acid may be exemplified. Among these, a (meth)acrylic acid alkyl ester monomer (the number of carbon atoms other than the (meth)acryloyl group is preferably in a range of 1 to 24, more preferably in a range of 1 to 12, and particularly preferably in a range of 1 to 8) is preferably and 2-hydroxyethyl (meth)acrylate, n-butyl (meth)acrylate, or tetraethylene glycol dimethacrylate is particularly preferable.

In the present specification, the term "acryl" or "acryloyl" indicates not only an acryloyl group but also a group having an induced structure thereof in a broad sense and is intended to include a structure having a specific substituent at the α-position of an acryloyl group. In this case, a structure having a hydrogen atom at the α-position is occasionally referred to as acryl or acryloyl in a narrow sense. A structure having a methyl group at the α-position is referred to as methacryl and this structure is occasionally referred to as (meth)acryl by indicating any of acryl (a hydrogen atom at the α-position) and methacryl (a methyl group at the α-position).

In an ethylenic monomer, the number of ethylenically unsaturated bonds in a molecule is not particularly limited, but is preferably in a range of 1 to 8, more preferably in a range of 1 to 4, and particularly preferably 1 or 2.

It is also preferable that a monomer forming a copolymer component is a compound represented by the following formula.

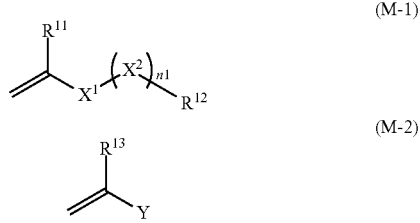

(M-1)

(M-2)

In the formulae, $R^{11}$ and $R^{13}$ represent a hydrogen atom, an alkyl group (the number of carbon atoms thereof is preferably in a range of 1 to 12, more preferably in a range of 1 to 6, and particularly preferably in a range of 1 to 3), a hydroxyl group, a cyano group, or a halogen atom. Among these, a hydrogen atom or a methyl group is preferable.

$X^1$ represents a single bond or a linking group. As the linking group, a hetero linking group of the following linking group La is preferable and —C(=O)—, —O—, —S—, —NR$^N$—, or a combination of these is more preferable. $R^N$ has the same definition as that for a group defined below. It is more preferable that $X^1$ represents —C(=O)O— or —C(=O)NR$^N$—.

$X^2$ represents a linking group. As $X^2$, the following linking group La is preferable and a hydrocarbon linking group is more preferable. Alternatively, a linking group which may have a monomer or oligomer structure of the linking group La is exemplified. Specific examples thereof include a (poly)alkyleneoxy group, a carbonyl (poly)oxyalkylene group, a carbonyl (poly)alkyleneoxy group, a carbonyloxy (poly)alkyleneoxy group, a (poly)alkyleneimino group, an alkylene (poly)iminoalkylene group, a carbonyl (poly)iminoalkylene group, a carbonyl (poly)alkyleneimino group, a (poly)ester group, and a (poly)amide group. A repetition number x at this time is preferably in the same range as described below, more preferably in a range of 1 to 20, and still more preferably in a range of 1 to 10. When $X^2$ represents a group which can have a substituent, $X^2$ may further have the following substituents T. Examples of other substituents include a hydroxyl group, a cyano group, a halogen atom, an alkoxy group, an acyl group, a carboxyl group (a salt or an ester thereof), a sulfonic acid group (a salt or an ester thereof), a phosphoric acid group (a salt or an ester thereof), and a phosphonic acid group (a salt or an ester thereof).

$R^{12}$ represents a hydrogen atom or any of the following substituents T. Among the examples of the substituents T, a hydrogen atom, a hydroxyl group, a halogen atom, an alkoxy group, an acyl group, an alkyl group, an alkenyl group, a (meth)acryloyl group, a (meth)acryloyloxy group, or a (meth)acryloylimino group is preferable. When $R^{12}$ represents a group which can have a substituent, $R^{12}$ may further have the following substituents T. Examples of other substituents include a hydroxyl group, a cyano group, a halogen atom, an alkoxy group, an acyl group, a carboxyl group (a salt or an ester thereof), a sulfonic acid group (a salt or an ester thereof), a phosphoric acid group (a salt or an ester thereof), and a phosphonic acid group (a salt or an ester thereof).

Y represents an alkyl group (the number of carbon atoms thereof is preferably in a range of 1 to 12, more preferably in a range of 1 to 6, and particularly preferably in a range of 1 to 3), an alkenyl group (the number of carbon atoms thereof is preferably in a range of 2 to 12 and more preferably in a range of 2 to 6), an alkynyl group (the number of carbon atoms thereof is preferably in a range of 2 to 12 and more preferably in a range of 2 to 6), an aryl group (the number of carbon atoms thereof is preferably in a range of 6 to 22, more preferably in a range of 6 to 14, and particularly preferably in a range of 6 to 10), an aralkyl group (the number of carbon atoms thereof is preferably in a range of 7 to 23, more preferably in a range of 7 to 15, and particularly preferably in a range of 7 to 11), a heteroaryl group, and a cyano group. Examples of the heteroaryl group are the same as those exemplified for the heterocyclic group of the following substituents T. Among those, a pyrrolidone group may be exemplified. When Y represents a group which can have a substituent, Y may further have the following substituents T. Examples of other substituents include a hydroxyl group, a cyano group, a halogen atom, an alkoxy group, an acyl group, a carboxyl group (a salt or an ester thereof), a sulfonic acid group (a salt or an ester thereof), a phosphoric acid group (a salt or an ester thereof), and a phosphoric acid group (a salt or an ester thereof).

n1 represents 0 or 1.

When the specific polymer compound (A) is a copolymer, the content (copolymerization ratio) of the specific sulfobetaine monomer (monomer represented by Formula (I) or (II)) is preferably 1% or greater, more preferably 5% or greater, still more preferably 10% or greater, and particularly preferably 20% or greater on a mass ratio basis. The upper limit thereof is preferably 95% or less, more preferably 90% or less, and particularly preferably 80% or less. In the case where the specific polymer compound (A) is a copolymer, the content of the copolymer component is preferably 5 parts or greater, more preferably 20 parts or greater, and particularly preferably 40 parts or greater on a mass ratio basis when the content of the specific sulfobetaine monomer is set to 100 parts. The upper limit thereof is preferably 10000 parts or less, more preferably 3000 or less, and particularly preferably 1000 or less. Each of the specific sulfobetaine monomer and the copolymer component can be used alone or in combination of two or more kinds thereof.

As described above, it is believed that the repeating unit of the polymer compound (A) which is derived from a specific sulfobetaine monomer exhibits desired effects when used as a material non-adhesive to a biological substance through the balance of the charge thereof, hydrophobicity of a partial structure thereof, or a network formed by the polymer compound. Such an action can be suitably used depending on the applications or desired performance. Such high versatility is one of the advantages of the present invention. Specifically, a curable resin composition suitable for a coating solution or a structural material having fluidity can be also obtained. If necessary, photosensitivity can be imparted or a surface graft polymer grown on the surface of a member can be also obtained. Even at this time, the above-described specific action can be obtained and excellent performance can be exhibited. In other words, the type or the amount of the compound forming the copolymer component is not limited and can be widely applied as various forms of materials. The same can be applied to other components or media contained in the composition and the type can be suitably selected according to the needs. Further, the present invention is not excessively and limitatively interpreted by this description.

The display of compounds in the present specification (for example, when a compound or a monomer is referred to by being added at the end) is used to include the compound itself, a salt thereof, and an ion thereof. Further, the display thereof includes a derivative which is partially changed by introducing a substituent within a range in which desired effects can be exhibited.

A substituent (the same applies to a linking group) in which substitution or unsubstitution is not specified in the present specification means that an arbitrary substituent may be included in the group within a range in which desired effects can be exhibited. The same applies to a compound in which substitution or unsubstitution is not specified. As a preferred substituent, the substituents T described below are exemplified.

Examples of the substituents T include an alkyl group (preferably an alkyl group having 1 to 20 carbon atoms such as methyl, ethyl, isopropyl, t-butyl, pentyl, heptyl, 1-ethylpentyl, benzyl, 2-ethoxyethyl, or 1-carboxymethyl), an alkenyl group (preferably, an alkenyl group having 2 to 20 carbon atoms such as vinyl, allyl, or oleyl), an alkynyl group (preferably an alkynyl group having 2 to 20 carbon atoms such as ethynyl, butadiynyl, or phenylethynyl), a cycloalkyl group (preferably a cycloalkyl group having 3 to 20 carbon atoms such as cyclopropyl, cyclopentyl, cyclohexyl, or 4-methylcyclohexyl, and in this case, when a group is referred to as an alkyl group in the present specification, the meaning of this group typically includes a cycloalkyl group), an aryl group (preferably an aryl group having 6 to 26 carbon atoms such as phenyl, 1-naphthyl, 4-methoxyphenyl, 2-chlorophenyl, or 3-methylphenyl), a heterocyclic group (preferably a heterocyclic group having 2 to 20 carbon atoms or preferably a 5- or 6-membered heterocyclic group having at least one of an oxygen atom, a sulfur atom and a nitrogen atom such as tetrahydropyran, tetrahydrofuran, 2-pyridyl, 4-pyridyl, 2-imidazolyl, 2-benzimidazolyl, 2-thiazolyl, or 2-oxazolyl), a pyrrolidone group, an alkoxy group (preferably an alkoxy group having 1 to 20 carbon atoms such as methoxy, ethoxy, isopropyloxy, or benzyloxy), an aryloxy group (preferably an aryloxy group having 6 to 26 carbon atoms such as phenoxy, 1-naphthyloxy, 3-methylphenoxy, or 4-methoxyphenoxy), an alkoxycarbonyl group (preferably an alkoxycarbonyl group having 2 to 20 carbon atoms such as ethoxycarbonyl or 2-ethylhexyloxycarbrbonyl), an aryloxycarbonyl group (preferably an aryloxycarbonyl group having 6 to 26 carbon atoms such as phenoxycarbonyl, 1-naphthyloxycarbonyl, 3-methylphenoxycarbonyl, or 4-methoxyphenoxycarbonyl), an amino group (preferably an amino group having 0 to 20 carbon atoms, an alkylamino group having 0 to 20 carbon atoms, or an acylamino group having 0 to 20 carbon atoms such as amino, N,N-dimethylamino, N,N-diethylamino, N-ethylamino, or anilino), a sulfamoyl group (preferably a sulfamoyl group having 0 to 20 carbon atoms such as N,N-dimethylsulfamoyl or N-phenylsulfamoyl), an acyl group (preferably an acyl group having 1 to 20 carbon atoms such as acetyl, propionyl, or butyryl), an aryloyl group (preferably an aryloyl group having 7 to 23 carbon atoms such as a benzoyl group, and in this case, when a group is referred to as an acyl group in the present specification, the meaning of this group typically includes an aryloyl group), an acyloxy group (preferably an acyloxy group having 1 to 20 carbon atoms such as acetyloxy), an aryloyloxy group (preferably an aryloyloxy group having 7 to 23 carbon atoms such as benzoyloxy, and in this case, when a group is referred to as an acyloxy group in the present specification, the meaning of this group typically includes an aryloyloxy group), a carbamoyl group (preferably a carbamoyl group having 1 to 20 carbon atoms such as N,N-dimethylcarbamoyl or N-phenylcarbamoyl), an acylamino group (preferably an acylamino group having 1 to 20 carbon atoms such as acetylamino or benzoylamino), an alkylthio group (preferably an alkylthio group having 1 to 20 carbon atoms such as methylthio, ethylthio, isopropylthio, or benzylthio), an arylthio group (preferably an arylthio group having 6 to 26 carbon atoms such as phenylthio, 1-naphthylthio, 3-methylphenylthio, or 4-methoxyphenylthio), an alkylsulfonyl group (preferably an alkylsulfonyl group having 1 to 20 carbon atoms such as methylsulfonyl or ethylsulfonyl), an arylsulfonyl group (preferably an arylsulfonyl group having 6 to 22 carbon atoms such as benzenesulfonyl), an alkylsilyl group (preferably an alkylsilyl group having 1 to 20 carbon atoms such as monomethylsilyl, dimethylsilyl, trimethylsilyl, or triethylsilyl), an arylsilyl group (preferably an arylsilyl group having 6 to 42 carbon atoms such as triphenylsilyl), an alkoxysilyl group (preferably an alkoxysilyl group having 1 to 20 carbon atoms such as monomethoxysilyl, dimethoxysilyl, trimethoxysilyl, or triethoxysilyl), an aryloxysilyl group (preferably an aryloxysilyl group having 6 to 42 carbon atoms such as triphenyloxysilyl), a phosphoryl group (preferably a phosphoryl group having 0 to 20 carbon atoms such as $-OP(=O)(R^P)_2$), a phosphonyl group (preferably a phosphonyl group having 0 to 20 carbon atoms such as $-P(=O)(R^P)_2$), a phosphinyl group (preferably a phosphinyl group having 0 to 20 carbon atoms such as $-P(R^P)_2$), a (meth)acryloyl group, a (meth)acryloyloxy group, a (meth) aryloylimino group ((meth)acrylamide group), a hydroxyl group, a thiol group, a carboxyl group, a phosphoric acid group, a phosphonic acid group, a sulfonic acid group, a cyano group, and a halogen atom (such as a fluorine atom, a chlorine atom, a bromine atom, or an iodine atom).

Moreover, respective groups exemplified in these substituents T may be further substituted with the above-described substituents T.

Further, the substituents are acidic groups or basic groups, salts thereof may be formed.

When a compound or a substituent and a linking group include an alkyl group, an alkylene group, an alkenyl group, an alkenylene group, an alkynyl group, or an alkynylene group, these may be cyclic, chain-like, linear, or branched and may be substituted or unsubstituted as described above.

Each substituent defined in the present specification may be substituted through the following linking group La within a range in which effects of the present invention are exhibited or may include the linking group La in the structure thereof. For example, an alkyl group, an alkylene group, an alkenyl group, or an alkenylene group may include the following hetero linking group in the structure thereof.

As the linking group La, a hydrocarbon linking group [an alkylene group having 1 to 10 carbon atoms (the carbon atoms is more preferably in a range of 1 to 6 and still more preferably in a range of 1 to 3), an alkenylene group having 2 to 10 carbon atoms (the number of carbon atoms is more preferably in a range of 2 to 6 and still more preferably in a range of 2 to 4), an alkynylene group having 2 to 10 carbon atoms (the number of carbon atoms is more preferably in a range of 2 to 6 and still more preferably in a range of 2 to 4), an arylene group having 6 to 22 carbon atoms (the number of carbon atoms is more preferably in a range of 6 to 10), or a combination of these], a hetero linking group [a carbonyl group (—CO—), a thiocarbonyl group (—CS—), an ether group (—O—), a thioether group (—S—), an imino group (—$NR^N$—), an imine linking group ($R^N$—N=C<, —N=C($R^N$)—), a sulfonyl group (—$SO_2$—), a sulfinyl group (—SO—), a phosphoric acid linking group (—O—P(OH)(O)—O—), a phosphonic acid linking group (—P(OH)(O)—O—), or a combination of these], or a linking group formed by combining these is preferable. Further, in a case where a substituent or a linking group is fused to form a ring, the above-described hydrocarbon linking group may appropriately form a double bond or a triple bond for linkage. As a ring to be formed, a 5- or 6-membered ring is preferable. A nitrogen-containing 5-membered ring is preferable as a 5-membered ring, and examples of the compound that forms the ring include pyrrole, imidazole, pyrazole, indazole, indole, benzimidazole, pyrrolidine, imidazolidine, pyrazolidine, indoline, carbazole, and derivatives of these. Examples of a 6-membered ring include piperidine, morpholine, piperazine, and derivatives of these. Further, when an aryl group, a heterocyclic group, and the like are included, these may be a single ring or a fused ring and may be substituted or unsubstituted.

$R^N$ represents a hydrogen atom or a substituent. Preferred examples of the substituent include an alkyl group (the number of carbon atoms thereof is preferably in a range of 1 to 24, more preferably in a range of 1 to 12, still more preferably in a range of 1 to 6, and particularly preferably in a range of 1 to 3), an alkenyl group (the number of carbon atoms thereof is preferably in a range of 2 to 24, more preferably in a range of 2 to 12, still more preferably in a range of 2 to 6, and particularly preferably 2 or 3), an alkynyl group (the number of carbon atoms thereof is preferably in a range of 2 to 24, more preferably in a range of 2 to 12, still more preferably in a range of 2 to 6, and particularly preferably 2 or 3), an aralkyl group (the number of carbon atoms thereof is preferably in a range of 7 to 22, more preferably in a range of 7 to 14, and particularly preferably 7 to 10), and an aryl group (the number of carbon atoms thereof is preferably in a range of 6 to 22, more preferably in a range of 6 to 14, and particularly preferably in a range of 6 to 10).

$R^P$ represents a hydrogen atom, a hydroxyl group, or a substituent. Preferred examples of the substituent include an alkyl group (the number of carbon atoms thereof is preferably in a range of 1 to 24, more preferably in a range of 1 to 12, still more preferably in a range of 1 to 6, and particularly preferably in a range of 1 to 3), an alkenyl group (the number of carbon atoms thereof is preferably in a range of 2 to 24, more preferably in a range of 2 to 12, still more preferably in a range of 2 to 6, and particularly preferably 2 or 3), an alkynyl group (the number of carbon atoms thereof is preferably in a range of 2 to 24, more preferably in a range of 2 to 12, still more preferably in a range of 2 to 6, and particularly preferably 2 or 3), an aralkyl group (the number of carbon atoms thereof is preferably in a range of 7 to 22, more preferably in a range of 7 to 14, and particularly preferably 7 to 10), an aryl group (the number of carbon atoms thereof is preferably in a range of 6 to 22, more preferably in a range of 6 to 14, and particularly preferably in a range of 6 to 10), an alkoxy group (the number of carbon atoms thereof is preferably in a range of 1 to 24, more preferably in a range of 1 to 12, still more preferably in a range of 1 to 6, and particularly preferably in a range of 1 to 3), an alkenyloxy group (the number of carbon atoms thereof is preferably in a range of 2 to 24, more preferably in a range of 2 to 12, still more preferably in a range of 2 to 6, and particularly preferably 2 or 3), an alkynyloxy group (the number of carbon atoms is preferably in a range of 2 to 24, more preferably in a range of 2 to 12, still more preferably in a range of 2 to 6, and particularly preferably in a range of 2 or 3), an aralkyloxy group (the number of carbon atoms thereof is preferably in a range of 7 to 22, more preferably in a range of 7 to 14, and particularly preferably in a range of 7 to 10), and an aryloxy group (the number of carbon atoms thereof is preferably in a range of 6 to 22, more preferably in a range of 6 to 14, and particularly preferably in a range of 6 to 10).

The number of atoms constituting the linking group La is preferably in a range of 1 to 36, more preferably in a range of 1 to 24, still more preferably in a range of 1 to 12, and particularly preferably in a range of 1 to 6. The number of linking atoms of the linking group is preferably 10 or less and more preferably 8 or less. The lower limit thereof is 1 or greater. The number of linking atoms indicates the minimum number of atoms that are positioned in a path connecting predetermined structural units to each other and are involved in the linkage. For example, in a case of —$CH_2$—C(=O)—O—, the number of atoms constituting the linking group is 6, but the number of linking atoms is 3.

Specific examples of the combination of linking groups include the followings: an oxycarbonyl group (—OCO—), a carbonate group (—OCOO—), an amide group (—CONH—), a urethane group (—NHCOO—), a urea group (—NHCONH—), a (poly)alkyleneoxy group (—(Lr—O)x-), a carbonyl (poly)oxyalkylene group (—CO—(O—Lr)x-), a carbonyl (poly)alkyleneoxy group (—CO—(Lr—O)x-), a carbonyloxy (poly)alkyleneoxy group (—COO—(Lr—O)x-), a (poly)alkyleneimino group (—(Lr—$NR^N$)x), an alkylene (poly)iminoalkylene group (—Lr—(NR$^N$—Lr)x-), a carbonyl (poly)iminoalkylene group (—CO—(NR$^N$—Lr)x-), a carbonyl (poly)alkyleneimino group (—CO—(Lr—NR$^N$)x-), a (poly)ester group (—(CO—O—Lr)x-, —(O—CO—Lr)x-, —(O—Lr—CO)x-, —(Lr—CO—O)x-, or —(Lr—O—CO)x-), and a (poly)amide group (—(CO—NR$^N$—Lr)x-, —(NR$^N$—CO—Lr)x-, —(N—Lr—C—O)x-, —(Lr—CO—NR$^N$)x-, or —(Lr—NR$^N$—CO)x-). x represents an integer of 1 or greater, and is preferably in a range of 1 to 500 and more preferably in a range of 1 to 100.

It is preferable that Lr represents an alkylene group, an alkenylene group, or an alkynylene group. The number of carbon atoms of Lr is preferably in a range of 1 to 12, more preferably in a range of 1 to 6, and particularly preferably in a range of 1 to 3. A plurality of Lr's, R$^N$'s, R$^P$'s, or x's are not necessarily the same as each other. The orientation of a linking group is not limited to the order described above, and it may be understood that the orientation thereof appropriately matches the orientation shown in a predetermined chemical formula.

[Synthesis of Polymer (Polymer Compound A)]

A method of producing the material non-adhesive to a biological substance of the present invention is not particularly limited, and the material can be produced according to a conventional method. In other words, the polymer compound (A) can be synthesized by a typical polymerization method. In addition, a composition thereof can be prepared by adding arbitrary components as necessary and mixing the components.

The method of producing a polymer (polymer compound A) may follow a conventional method. For example, the polymer is obtained by reacting a specific sulfobetaine monomer with a monomer forming a copolymer component in a solvent in the presence of a polymerization initiator. This unreacted monomer-containing composition becomes a curable composition for forming a material non-adhesive to a biological substance. The solvent to be used here is not limited as long as each monomer is dissolved therein. Specifically, water or an organic solvent described in the section of (a material non-adhesive to a liquid composition type biological substance) below may be exemplified. As the polymerization initiator, a typical radical initiator can be used. Examples thereof include an azo compound such as 2,2'-azobisisobutyronitrile (AIBN), 3-carboxypropionitrile, 2,2'-azobis(2,4-dimethylvaleronitrile), or dimethyl-(2,2')-azobis(2-methylpropionate) [V-601], an organic peroxide such as benzoyl peroxide, lauroyl peroxide, or potassium persulfate, a mixture of 1-hydroxy-cyclohexyl-phenyl-ketone and benzophenone at a weight ratio of 1:1, and an alkylphenone-based compound such as 2-hydroxy-2-methyl-1-phenyl-propane-1-one, 1-[4-(2-hydroxyethoxy)phenyl]-2-hydroxy-2-methylpropan-1-one, or 2-hydroxy-1-(4-(2-(2-hydroxyethoxy)ethoxy)phenyl)-2-methylpropan-1-one. A polymerization initiator described in the section of (a material non-adhesive to a curable resin composition type biological substance) can be also suitably employed as the polymerization initiator. In addition, a polymer (polymer compound A)-containing solution synthesized at this time or a cured film thereof can be used as the material non-adhesive to a biological substance.

[Curable Composition]

The curable composition of the present invention is a composition used to form the material non-adhesive to a biological substance and contains a sulfobetaine monomer represented by Formula (I) or (II). In the curable composition (monomer-containing composition containing a sulfobetaine monomer) serving as a raw material of the material non-adhesive to a biological substance, the amount of the monomer compound may be suitably set according to the reaction conditions for a polymerization reaction or usage, but the amount of the monomer compound in the solid components is preferably 20% by mass or greater, more preferably 30% by mass or greater, and particularly preferably 50% by mass or greater. The upper limit thereof is preferably 99% by mass or less, more preferably 95% by mass or less, and particularly preferably 90% by mass or less. Further, the "curable composition" described here is distinguished from a "material non-adhesive to a biological substance" described below. In other words, the former indicates a composition containing a sulfobetaine monomer in a state of an unpolymerized monomer. The latter indicates a material containing a polymer of a sulfobetaine monomer. The "curable composition" may be in a state of a liquid, paste, or a powder mixture, but it is preferable that the curable composition is in the form of being cured by a predetermined treatment (for example, a heating treatment or an exposure treatment). Further, a composition containing both of a polymer and a monomer of a sulfobetaine monomer is classified as a curable composition in a case where the monomer is a main component (the content thereof is greater than 50% by mass when the total mass of the polymer and the monomer is set to 100% by mass).

The curable composition serving as a raw material of the material non-adhesive to a biological substance may contain a monomer forming the above-described copolymer component, a solvent, or a polymerization initiator and is exemplified as a preferred embodiment. Further, as the monomer forming the copolymer component, the description made in the above-described copolymer component is preferably applied, and a monomer having an ethylenically unsaturated group is preferably applied. The relationship of the blending ratio between the copolymer component and the sulfobetaine monomer has the same definition as described above. The amount of a polymerization initiator may be typically extremely small and the amount thereof in the solid component is preferably in a range of 0.01% by mass to 3% by mass. As the type of solvent, it is preferable to select an organic solvent from the viewpoints of convenience of synthesis and applications of the material non-adhesive to a biological substance. The amount of the solvent is optional depending on the use or the like, but it is preferable that the solid component is adjusted to be 5% by mass or greater and more preferable that the solid content is adjusted to be 30% by mass or greater. The upper limit thereof is preferably 100% by mass or less and more preferably 70% by mass or less. The curable composition may suitably contain other components. Examples of other components include a binder polymer, a crosslinking agent, a polymerization inhibitor, a surfactant, a dispersant, and optional components.

[Material Non-Adhesive to Biological Substance]

As described above, the form of the material non-adhesive to a biological substance of the present invention is not particularly limited. The material may be in the form of a liquid, powder, a film (membrane), or the like. Among these, it is preferable that the material non-adhesive to a biological substance is a film or a resin composition used to form the film; or a structure or a resin composition used to form the structure. The amount of the polymer compound (A) in the material non-adhesive to a biological substance is not particularly limited, but the amount thereof in the solid component is preferably 10% by mass or greater, more preferably 20% by mass or greater, and still more preferably 30% by mass or greater. As the upper limit thereof, the amount of the polymer compound (A) may be 100% by mass (total amount). In a case where the material non-adhesive to a biological substance contains other components, the amount of the polymer compound (A) is preferably 90% by mass or less, more preferably 80% by mass or less, and still more preferably 70% by mass or less.

Further, the solid component (solid content) in the present specification indicates a component which is not lost because of volatilization or evaporation when subjected to a drying treatment at 100° C. for 6 hours under reduced pressure. The solid content typically indicates a component other than a solvent or a dispersion medium.

Molecular Weight

The weight average molecular weight of the polymer compound (A) can be prepared according to the purpose of use thereof. The weight average molecular weight thereof is preferably 1000 or greater, more preferably 5000 or greater, and particularly preferably 10000 or greater. The upper limit thereof is preferably 5000000 or less and more preferably 2000000 or less. In a case of the low molecular weight thereof, the upper limit thereof is preferably 1000000 or less, more preferably 500000 or less, still more preferably 200000 or less, even still more preferably 100000 or less, and particularly preferably 50000 or less. It is preferable that the weight average molecular weight of the polymer compound (A) is set to be sufficiently large because the molecular weight thereof is easily controlled and non-adhesive properties to a biological substance can be sufficiently exhibited. When the weight average molecular weight is set to be less than or equal to the above-described upper limit, the viscosity is maintained to be low so that the processability becomes excellent and the material can be compatible with solubility when the material is set to a liquid composition.

The molecular weight of the polymer compound (a polymer or an oligomer) in the present invention indicates the weight average molecular weight unless otherwise noted, and a value measured using gel permeation chromatography (GPC) in terms of standard polystyrene is employed. The measuring device and the measuring conditions are based on the following Condition 1, and Condition 2 is accepted depending on the solubility or the like of a sample. In this case, an appropriate carrier (eluent) and a column compatible with the carrier may be further selected and then used depending on the type of polymer. Other matters are will be determined with reference to JISK7252-1 to 4:2008. Further, a hardly soluble polymer compound is measured at a concentration in which the polymer compound is soluble under the following conditions.

(Condition 1)

Column: a column formed by connecting TOSOH TSKgel Super HZM-H, TOSOH TSKgel Super HZ4000, and TOSOH TSKgel Super HZ2000 (all trade names) to each other is used Carrier: tetrahydrofuran Measurement temperature: 40° C.

Flow rate of carrier: 1.0 ml/min

Concentration of sample: 0.1% by mass

Detector: refractive index (RI) detector

Injection volume: 0.1 ml (Condition 2)

Column: a column formed by connecting two of TOSOH TSKgel Super AWM-H (trade name) to each other is used Carrier: 10 mM LiBr/N-methylpyrrolidone Measurement temperature: 40° C.

Flow rate of carrier: 1.0 ml/min

Concentration of sample: 0.1% by mass

Detector: refractive index (RI) detector

Injection volume: 0.1 ml (Material Non-Adhesive to Liquid Composition Type Biological Substance)

It is preferable that the material non-adhesive to a biological substance of the present invention is set to a liquid composition (coating solution or the like) (the material non-adhesive to a biological substance of the present invention is a liquid composition type material). In this case, it is preferable that the above-described specific polymer compound (A) is dissolved in other liquid monomers in the composition or is dissolved or dispersed in water or an organic solvent. In the present invention, an organic solvent is preferable when applications of the material non-adhesive to a biological substance are considered. Alternatively, the solution after the above-described polymerization reaction may be used as it is. Examples of the organic solvent include an aliphatic compound, a halogenated hydrocarbon compound, an alcohol compound, an ether compound, an ester compound, a ketone compound, a nitrile compound, an amide compound, a sulfoxide compound, and an aromatic compound, and these solvents may be mixed with each other and then used. Respective examples are shown below.

Aliphatic Compound

Hexane, heptane, cyclohexane, methylcyclohexane, octane, pentane, cyclopentane, or the like Halogenated Hydrocarbon Compound Methylene chloride, chloroform, dichloromethane, ethane dichloride, carbon tetrachloride, trichloroethylene, tetrachloroethylene, epichlorohydrin, monochlorobenzene, orthodichlorobenzene, allyl chloride, HCFC (hydrochlorofluorocarbon), methyl monochloroacetate, ethyl monochloroacetate, trichloroacetic acid monochloroacetate, methyl bromide, methyl iodide, or the like Alcohol Compound Methanol, ethanol, 1-propanol, 2-propanol, 2-butanol, ethylene glycol, propylene glycol, glycerin, 1,6-hexanediol, cyclohexanediol, sorbitol, xylitol, 2-methyl-2,4-pentanediol, 1,3-butanediol, 1,4-butanediol, hexafluoroisopropanol, or the like Ether Compound (Including a Hydroxyl Group-Containing Ether Compound)

Dimethyl ether, diethyl ether, diisopropyl ether, dibutyl ether, t-butyl methyl ether, cyclohexyl methyl ether, anisole, tetrahydrofuran, diethylene glycol, dipropylene glycol, triethylene glycol, polyethylene glycol, alkylene glycol alkyl ether (ethylene glycol mono(di)ethyl ether, ethylene glycol mono(di)butyl ether, propylene glycol mono(di)methyl ether, diethylene glycol mono(di)methyl ether, propylene glycol mono(di)methyl ether, dipropylene glycol mono(di)ethyl ether, tripropylene glycol mono(di)ethyl ether, diethylene glycol mono(di)butyl ether, or diethylene glycol mono(di)butyl ether), or the like Further, when a compound is referred to as a compound with "mono(di)" in the present specification, this indicates either of a compound with "mono" which has one substituent or a compound with "di" which has two substituents.

Ester Compound

Ethyl acetate, ethyl lactate, 2-(1-methoxy)propyl acetate, propylene glycol monomethyl ether acetate, or the like Ketone Compound Acetone, methyl ethyl ketone, methyl isobutyl ketone, cyclohexane, 2-heptanone, or the like Nitrile Compound Acetonitrile or the like Amide Compound N,N-dimethylformamide, 1-methyl-2-pyrrolidone, 2-pyrrolidinone, 1,3-dimethyl-2-imidazolidinone, ε-caprolactam, formamide, N-methylformamide, acetamide, N-methylacetamide, N,N-dimethylacetamide, N-methylpropanamide, hexamethylphosphoric triamide, or the like Sulfoxide Compound Dimethyl sulfoxide or the like Aromatic Compound Benzene, toluene, or the like The amount of the solvent to be used may be suitably set according to the use thereof, but it is preferable that the solid component containing the above-described specific polymer compound (A) is adjusted to be 5% by mass or greater and more preferable that the solid component containing the above-described specific polymer compound (A) is adjusted to be 30% by mass or greater. The upper limit thereof is preferably 100% by mass or less and more preferably 70% by mass or less. The solvent may be used alone or in combination of two or more kinds thereof.

(Material Non-Adhesive to Curable Resin Composition Type Biological Substance)

It is preferable that the material non-adhesive to a biological substance of the present invention is set to a curable resin composition (the material non-adhesive to a biological substance of the present invention is a curable resin composition type material). In this case, it is preferable that the above-described specific polymer compound (A), a polymerizable compound, and a polymerization initiator are mixed with each other. Further, organic solvents described in the paragraph above can be suitably used as the organic solvent. In addition, a crosslinking agent may be used as necessary.

Polymerizable Compound

In addition to the above-described monomers forming the copolymer component, monomers containing an epoxy group or an oxetanyl group may be exemplified as the polymerizable compound. The content of the polymerizable compound is preferably 1% by mass or greater, more preferably 3% by mass or greater, and still more preferably 5% by mass or greater with respect to the total solid content of the curable resin composition. The upper limit thereof is preferably 50% by mass or less, more preferably 40% by mass or less, and still more preferably 30% by mass or less. The polymerizable compound can be used alone or in combination of two or more kinds thereof.

Binder Polymer

In a case where the material non-adhesive to a biological substance is used as a composition, a binder polymer may be contained therein as a combination. As the binder polymer, a linear organic polymer may be used. Such a linear organic polymer is selected according to the use thereof and then used. For example, water development becomes possible when a water-soluble organic polymer is used. Examples of such linear organic polymer include radical polymers having a carboxylic acid group in the side chain thereof described in JP1984-44615A (JP-S59-44615A), JP1979-34327B (JP-S54-34327B), JP1983-12577B (JP-S58-12577B), JP1979-25957B (JP-S54-25957B), JP1979-92723A (JP-S54-92723A), JP1984-53836A (JP-S59-53836A), and JP1984-71048A (JP-S59-71048A). Specific examples thereof include a resin formed by singly polymerizing or copolymerizing a monomer having a carboxyl group; a resin formed by singly polymerizing or copolymerizing a monomer having an acid anhydride and hydrolyzing, half-esterifying, or half-amidating the acid anhydride unit; and epoxy acrylate formed by modifying an epoxy resin using an unsaturated monocarboxylic acid and an acid anhydride. Examples of the monomer having a carboxyl group include acrylic acid, methacrylic acid, itaconic acid, crotonic acid, maleic acid, fumaric acid, and 4-carboxyl styrene. Examples of the monomer having an acid anhydride include maleic anhydride.

Further, similarly, an acidic cellulose derivative having a carboxy group in the side chain thereof may be exemplified. In addition to this, a polymer having a hydroxyl group, to which a cyclic acid anhydride or the like is added, is useful.

The weight average molecular weight of the binder polymer is preferably 5000 or greater and more preferably in a range of 10000 to 300000. The polydispersity (weight average molecular weight/number average molecular weight) is preferably 1 or greater and more preferably in a range of 1.1 to 10. The binder polymer may be any of a random polymer, a block polymer, or a graft polymer.

The content of the binder polymer is preferably 1% by mass or greater, more preferably 3% by mass or greater, and still more preferably 4% by mass or greater with respect to the total solid content of the composition. The upper limit thereof is preferably 40% by mass or less, more preferably 30% by mass or less, and still more preferably 20% by mass or less. The binder polymer may be used alone or in combination of two or more kinds thereof.

Polymerization Initiator

A polymerization initiator is a compound that initiates and promotes polymerization of a polymerizable compound. A polymerization initiator may initiate polymerization using heat or initiate polymerization using light.

Examples of the polymerization initiator include an organic halogenated compound, an oxydiazole compound, a carbonyl compound, a ketal compound, a benzoin compound, an acridine compound, an organic peroxide compound, an azo compound, a coumarin compound, an azide compound, a metallocene compound, a hexaarylbiimidazole compound, an organic boric acid compound, a disulfonic acid compound, an oxime compound, an onium salt compound, a hydroxyacetophenone compound, an aminoacetophenone compound, an acylphosphine compound, and a phosphine oxide compound. As the specific examples thereof, the description after the paragraph [0135] of JP2010-106268A (paragraph [0163] of US2011/0124824A corresponding thereto) can be referred to and the contents of which are incorporated herein.

Specific examples of an acylphosphine oxide-based initiator include those described in JP4225898B. As an acylphosphine-based initiator, IRGACURE-819, DAROCUR 4265, and DAROCUR-TPO (trade names, all manufactured by BASF Corporation), which are commercially available, can be used.

As a hydroxyacetophenone-based initiator, IRGACURE-184, DAROCUR-1173, IRGACURE-500, IRGACURE-2959, IRGACURE-127 (trade names, all manufactured by BASF Corporation), and 2-hydroxy-1-(4-(2-(2-hydroxyethoxy)ethoxy)phenyl)-2-methylpropan-1-one can be used.

Examples of an aminoacetophenone-based initiator include those described in JP-1998-291969A (JP-H10-291969A). As the aminoacetophenone-based initiator, IRGACURE-907, IRGACURE-369, and IRGACURE-379 (trade names, all manufactured by BASF Corporation), which are commercially available, can be used. As the aminoacetophenone-based initiator, compounds described in JP2009-191179A in which the absorption wavelength is matched to a long wave light source having a wavelength of 365 nm or 405 nm can be used.

An oxime compound has a function as a thermal polymerization initiator which is decomposed by heat and initiates and promotes polymerization. The oxime compound is less colored by post-heating and curability is also excellent. As the oxime compound, a compound having the maximum absorption wavelength in a wavelength region of 350 nm to 500 nm is preferable, a compound having the maximum absorption wavelength in a wavelength region of 360 nm to 480 nm is more preferable, and a compound having high absorbance at wavelengths of 365 nm and 455 nm is particularly preferable. As the oxime compound, IRGACURE OXE01 and IRGACURE OXE02 (trade names, both manufactured by BASF Corporation), which are commercially available, can be suitably used.

The content of the polymerization initiator is preferably 0.1% by mass or greater, more preferably 0.3% by mass or greater, and still more preferably 0.5% by mass or greater with respect to the total solid content of the composition. The upper limit thereof is preferably 10% by mass or less, more preferably 8% by mass or less, and still more preferably 5% by mass or less. The polymerization initiator may be used alone or in combination of two or more kinds thereof.

Crosslinking Agent

Examples of the crosslinking agent include di(meth)acrylate such as ethylene glycol di(meth)acrylate, 1,4-butanediol di(meth)acrylate, neopentyl glycol di(meth)acrylate, 1,6-hexanediol di(meth)acrylate, nonanediol di(meth)acrylate, trans-1,4-cyclohexanediol di(meth)acrylate, polyethylene glycol di(meth)acrylate, or polypropylene glycol di(meth)acrylate; tri(meth)acrylate such as trimethylolpropane tri(meth)acrylate or pentaerythritol tri(meth)acrylate; tetrafunctional or pentafunctional (meth)acrylate such as pentaerythritol tetra(meth)acrylate or dipentaerythritol hexa(meth)acrylate; and polyfunctional acrylamide such as polymerizable compounds 1 to 12 described in paragraph [0031] of JIII Journal of Technical Disclosure (public technical No. 2013-502654 issued on Aug. 27, 2013, Japan Institute for Promoting Invention and Innovation), polyfunctional compounds 1 to 11 and N-(2-acetamideethyl)-N-(2-hydroxyethyl)acrylamide described in paragraph [0192] of Japan Institute of Invention and Innovation (public technical No. 2013-502654 issued on Aug. 27, 2013, Japan Institute for Promoting Invention and Innovation).

Among these, di(meth)acrylate is preferable and polyethylene glycol di(meth)acrylate, polypropylene glycol di(meth)acrylate, trimethylol propane tri(meth)acrylate, or pentaerythritol (meth)acrylate is more preferable. The crosslinking agent may be used alone or in combination of two or more kinds thereof.

The content of the crosslinking agent is preferably in a range of 0.1 to 70% by mass with respect to the total mass of the composition.

Polymerization Inhibitor

In addition, the material may contain a polymerization inhibitor as necessary. In order to prevent unnecessary polymerization of a compound having a polymerizable ethylenically unsaturated double bond during production or storage, it is preferable that a polymerization inhibitor is added. Examples of the polymerization inhibitor include a phenolic hydroxyl group-containing compound, N-oxide compounds, piperidine 1-oxyl free radical compounds, pyrrolidine 1-oxyl free radical compounds, N-nitrosophenylhydroxylamines, diazonium compounds, cationic dyes, sulfide group-containing compounds, nitro group-containing compounds, and transition metal compounds such as $FeCl_3$ and $CuCl_2$. As the specific examples of the polymerization inhibitor, the description in paragraphs [0260] to [0280] of JP2010-106268A (paragraphs [0284] to [0296] of US2011/0124824A corresponding thereto) can be referred to and the contents of which are incorporated herein.

The amount of the polymerization inhibitor is preferably 0.01 parts by mass or greater and particularly preferably 0.05 parts by mass or greater with respect to 100 parts by mass of the polymerization initiator. The upper limit thereof is preferably 10 parts by mass or less, more preferably 8 parts by mass or less, and particularly preferably 5 parts by mass or less. The polymerization inhibitor can be used alone or in combination of two or more kinds thereof.

Surfactant

In a case where the material non-adhesive to a biological substance is used as a composition, a surfactant may be added thereto. As the surfactant, various surfactants such as a fluorine-based surfactant, a non-ionic surfactant, a cationic surfactant, an anionic surfactant, and a silicone-based surfactant can be used. The amount of the surfactant to be added is preferably 0.001% by mass or greater and more preferably 0.005% by mass or greater with respect to the total mass of the composition. The upper limit thereof is preferably 2% by mass or less and more preferably 1% by mass or less. The surfactant may be used alone or in combination of two or more kinds thereof.

Dispersant

In the case where the material non-adhesive to a biological substance is used as a composition, a dispersant may be added thereto. Examples thereof include a polymer dispersant. The polymer dispersant may have a structure of a block copolymer or a structure of a graft polymer. The weight average molecular weight of the polymer dispersant is preferably in a range of 3000 to 100000 and more preferably in a range of 5000 to 55000.

The content of the dispersant is preferably 1% by mass or greater, more preferably 3% by mass or greater, and particularly preferably 10% by mass or greater with respect to the total solid content of the composition. The upper limit thereof is preferably 50% by mass or less, more preferably 40% by mass or less, and still more preferably 30% by mass or less. The dispersant may be used alone or in combination of two or more kinds thereof.

The above-described composition may further contain optional components other than the above-described components as necessary. Examples of the optional components include additives such as a chain transfer agent, a sensitizing dye, a surface lubricant, a leveling agent, an antioxidant, a corrosion inhibitor, a light stabilizer, a UV absorber, a silane coupling agent, an inorganic or organic filler, powder such as metal powder or a pigment, a particulate material, and a foil-like material. The additives can be suitably added according to the use of various additives to be commonly used.

(Surface Graft Polymerization Method)

A surface graft polymerization method typically indicates a surface modification method of forming a polymer directly bonded to a substrate. For example, active species such as radicals are generated by irradiating the surface of the substrate with light and a monomer is polymerized from the surface of the substrate using the generated active species as the starting point. The surface graft polymerization method is used in the field of the hydrophilic film, the artificial blood vessel, or the like as a hydrophilic treatment applied to the surface of the substrate or a technique of controlling the adhesiveness of a biological substance.

According to the surface graft polymerization method, since a polymer to be generated and the substrate are typically bonded to each other through a covalent bond or the like, the generated polymer layer is brought into close contact with the substrate in an extremely strong state. Further, the polymer layer can be selected separately from the properties of the substrate and various kinds of polymer capable of expressing target functions can be widely selected.

In the present invention, the material non-adhesive to a biological substance may be formed using the above-described surface graft polymerization method. For example, the material non-adhesive to a biological substance may be formed by performing a surface treatment on a metal substrate such as a Co—Cr alloy, applying the above-described curable composition containing a specific sulfobetaine monomer thereto, and growing a polymer chain. The polymerization method at this time is not particularly limited, and a photoradical polymerization method or an atom transfer radical polymerization method can be used.

In regard to the surface graft polymerization method, for example, the description in J. Am. Chem. Soc. 205, 127, pp. 15843 to 15847 or the like can be referred to.

As described above, the meaning of the "biological substance" in the "material non-adhesive to a biological substance" of the present invention includes a material constituting an organism or a material related to an organism in a broad sense. Particularly, it is preferable that the "material non-adhesive to a biological substance" of the present invention is non-adhesive to protein, peptides, cells, tissues formed by cells being collected, or blood corpuscles, more preferable that the material is non-adhesive to protein, cells, tissues formed by cells being collected, or blood corpuscles, and particularly preferable that the material is non-adhesive to protein or cells.

The material non-adhesive to a biological substance of the present invention can be preferably used for medical instruments and artificial organs. Hereinafter, the outline of each application to which the material non-adhesive to a biological substance of the present invention can be applied will be described. The material non-adhesive to a biological substance of the present invention can be used by being added to a resin composition serving as a material of each application or being applied to the surface thereof to obtain a coating film. Particularly, it is preferable that the material non-adhesive to a biological substance is used as a coating film. Among the applications of the material, artificial organs and medical instruments including the material non-adhesive to a biological substance of the present invention in at least a part thereof are preferably provided.

Artificial Blood Vessel

Artificial blood vessels are mainly used for bypassing or shunting blood vessels by replacing pathological and biological blood vessels in a case of adults. In a case of children, the artificial blood vessels are mainly used for shunting or rebuilding blood vessels in many cases. The blood passes through the lumen of artificial blood vessels and the shape of the artificial blood vessels is tubular. As the quality of the artificial blood vessels, ease of use, no blood clots, suitability for organisms, functioning for a long term, and safe use are considered. In order to prevent blood clots, carcinogenicity, and deterioration, it is desirable that adhesion of blood or a biological substance contained in the blood is suppressed. It is desirable that the artificial blood vessels are inexpensive.

When artificial blood vessels are classified as materials, examples of the materials include a material made of cloth, a material made of polytetrafluoroethylene (PTFE), a biological substance, a synthetic polymer material, and a hybrid material formed by combining an artificial material and a biological substance. The material non-adhesive to a biological substance of the present invention can be used by being added to a resin composition serving as a material thereof or being applied to the surface thereof to obtain a coating film. Particularly, it is preferable that the material non-adhesive to a biological substance is used as a coating film.

In regard to the specific structures or production methods, the descriptions in JP2001-129000A, JP1993-023362A (JP-H05-023362A), and JP1998-506036A (JP-H10-506036A) can be referred to.

Hemodialysis Membrane

The hemodialysis is a method for treating people having a kidney whose function is abolished. Treatments of removing wastes, removing moisture, adjusting an electrolyte, maintaining the pH of blood to be constant, and the like are performed through the dialysis membrane. The treatments are performed by the blood and the dialysate being brought into contact with each other in a dialyzer. A thin membrane which is referred to as a semipermeable membrane is included in the dialyzer. In many cases, tens of thousands of hallow fiber membranes having a diameter of several hundreds of micrometers are bundled and used. Examples of the material of the dialysis membrane include a cellulose-based resin, polymethyl methacrylate (PMMA), polyacrylonitrile (PAN), polystyrene (PS), and polyethersulfone (PES). The material non-adhesive to a biological substance of the present invention can be used as the above-described material or by being applied to the surface thereof to obtain a coating film.

In regard to the specific structures or production methods, the descriptions in JP2004-313359A, JP2009-240499A, and JP1998-212347A (JP-H10-212347A) can be referred to.

Catheter

A catheter is a soft hallow tube and used by being inserted into body cavities such as chest cavities or abdominal cavities, the luminal portion such as the gastrointestinal tract or the ureter, or the blood vessel. Therefore, the catheter is used for discharge of the body fluid or injection infusion of a chemical liquid or a contrast medium. The thickness or the material thereof varies depending on the use thereof. The catheter used in the blood vessel is reinforced by a wire mesh and occasionally improves torque transmission. In some cases, the treatment is performed by sending a coil for blocking a stent balloon for intravascular expansion through the catheter. The materials are mainly polymer compounds such as nylon, silicon, and TEFLON (registered trademark). As a typical example, a catheter having a thickness of approximately 1 to 10 mm and a length of several centimeters to 2 m may be exemplified, but the shape thereof varies depending on the use or the purpose as described above. The material non-adhesive to a biological substance of the present invention can be used as the above-described material or by being applied to the surface thereof to obtain a coating film.

In regard to the specific structures or production methods, the descriptions in JP2004-313359A, JP2009-240499A, and JP1998-212347A (JP-H10-212347A) can be referred to.

Artificial Organs

When the functions of the heart, the lung, the liver, the kidney, or the like are impaired, this results in various diseases. In a case of serious diseases, the patient's life may be in danger. Artificial internal organs are used as replacements of diseased organs. As the artificial internal organs, organs formed by using mechanical devices or biologically produced organs may be exemplified. Examples of the organs formed by using mechanical devices include artificial heart and valves thereof and examples of the biologically produced organs include cultured skins. In the present specification, in addition to the artificial internal organs, artificial bones and artificial joints are included in artificial organs. The artificial bones indicate artificial materials that compensate the defective parts of bones. Conventionally, materials having high affinity for human bodies, for example, metals such as titanium or tungsten and ceramics have been used as the artificial bones. In recent years, apatite or the like is used. The material non-adhesive to a biological substance of the present invention can be used by being mixed into a resin serving as the above-described material or being applied to the surface thereof to obtain a coating film. Alternatively, an artificial anus or an excretion device (pouch) may be exemplified.

In regard to the specific structures or production methods, the descriptions in JP2014-144162A, JP2014-080367A, JP2014-057713A, and JP2014-039835A can be referred to.

In the present specification, as a definition of the term, members to be incorporated in a human body for the purpose of treatment for a long term, such as artificial blood vessels, artificial bones, or stents are referred to as artificial organs in a broad sense as described above.

Contact Lenses

As the type of contact lenses, there are hard contact lenses and soft contact lenses. The contact lenses are formed of specific resins. The material non-adhesive to a biological substance of the present invention can be used as the material of the contact lenses. As a method of producing contact lenses, any of a lace cutting method (cutting and grinding method), a spin casting method (centrifugal rotary casting method), and a cast molding method may be used. As the material of soft contact lenses, any of a non-ionic material, an ionic material, a material having a low water content, and a material having a high water content may be used. As contact lenses using specific resins, lenses having methyl methacrylate as a main component and lenses using silicon rubber are exemplified. Recently, lenses having silyl-based methacrylate or fluorine-based methacrylate as a main component, in which the impact on eyes is alleviated, are used. As production methods or materials of contact lenses, the descriptions in JP2011-081394A, JP2006-003827A, JP2014-008695A, JP2013-222141A, JP2011-172916A, JP2006-249381A, and WO2006/095750A can be referred to.

In addition, the material non-adhesive to a biological substance of the present invention can be applied to medical instruments such as blood filters, blood storage packs, and stoma pouches. The material non-adhesive to a biological substance may be used as a material constituting the material of a medical instrument or used as a coating film. Alternatively, the material non-adhesive to a biological substance may be applied to various medical inspection instruments, sanitary products, and daily necessities that require sanitary care. Further, the material non-adhesive to a biological substance of the present invention can be used as a treatment solution for contact lenses (see JP1993-107512A (JP-H05-107512A), JP2000-147442A, or the like), a treatment solution for spectacle lenses (see JP1999-292938A (JP-H11-292938A)), or a dental coating material (see JP2004-194874A, JP2006-151850A, JP2011-153101A, JP1999-158051A (JP-H11-158051A), or the like). In the present specification, the meaning of the medical instrument includes the above-described catheter or dialysis membrane, endoscopes, echo probes, and various sanitary products in a broad sense.

EXAMPLES

Hereinafter, the present invention will be described in more detail with reference to examples, but the present invention is not limited to the examples described below. Further, "%" or "part" shown as the formulation or the blending amount in the examples is on a mass basis unless otherwise noted.

Synthesis Example of Compound Ex1

N-(3-dimethylaminopropyl)methacrylamide (manufactured by Wako Pure Chemical Industries, Ltd., 119.18 g), acetonitrile (manufactured by Wako Pure Chemical Industries, Ltd., 350 g), and p-methoxyphenol (manufactured by Wako Pure Chemical Industries, Ltd., 0.060 g) were added to a 1 L three-neck flask equipped with a stirring blade and a cooling pipe, and 95.32 g of 1,4-butanonesultone (manufactured by Wako Pure Chemical Industries, Ltd.) was added dropwise thereto for 30 minutes while the mixture was stirred. After the dropwise addition was finished, the mixture was heated at 80° C. for 5 hours. After the reaction yield, the reaction solution separated into two layers was allowed to stand at room temperature for 10 hours so that a white solid was deposited from the lower layer. The white solid was recovered by suction filtration in a nitrogen atmosphere and stirred and washed in 800 ml of acetone. After the white solid was washed, the suction filtration was repeated and drying was carried out, thereby obtaining a compound ex1 (192.15 g).

Synthesis Example of Compound Ex10

25.10 g of 3,3'-iminobis(N,N-dimethylpropylamine), 31.02 g of potassium carbonate, 100 g of ethyl acetate, and 50 g of water were weighed in a 300 ml three-neck flask equipped with a stirrer and a thermometer, and 11.76 g of acrylic acid chloride was added dropwise thereto for 30 minutes in an ice bath. The mixture was further stirred at 0° C. for 30 minutes and a white precipitate to be generated was separated by filtration. The organic layer was dried over anhydrous magnesium sulfate, and the solvent was distilled off under reduced pressure. The obtained yellow crude product was purified using alumina column chromatography (ethyl acetate/methanol development), thereby obtaining 7.73 g of N,N-bis(3-(dimethylamino)propyl)acrylamide.

7.73 g of N,N-bis(3-(dimethylamino)propyl)acrylamide obtained in the above, 3.0 mg of p-methoxyphenol, and 40 g of acetonitrile were weighed in a 200 ml three-neck flask equipped with a stirrer, a thermometer, and a reflux tube. 8.77 g of 1,4-butanesultone was added dropwise thereto at room temperature, and the mixture was heated to 80° C. and reacted for 4 hours. After natural cooling, the supernatant was removed by decantation, the generated white precipitate was re-slurried with 20 ml of methanol and 800 ml of ethyl acetate, and then the precipitate was recovered by suction filtration in a nitrogen atmosphere. The precipitate was dried in a pressure-reduced oven at 40° C., thereby obtaining 15.30 g of a white solid compound ex10 (the following formula). The NMR measurement results of the white solid compound are shown below.

$^1$H-NMR (400 MHz, D$_2$O): δ=6.62 ppm (a: 1H, t), 6.16 ppm, 5.79 ppm (b, c: 2H, 2 d), 3.40-3.15 ppm (d+e+f: 12H, m), 2.96 ppm (g: 12H, s), 2.84 ppm (h: 4H, t), 1.96-1.69 ppm (i+j+k: 12H, m)

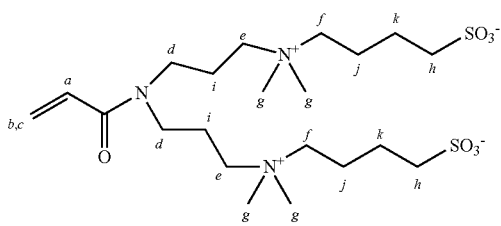

Example 1, Reference Example 1 and Comparative Example 1

(Synthesis of Polymer 1)

The compound ex1 (20 g) and ethanol (manufactured by Wako Pure Chemical Industries, Ltd., 40 g) were weighed in a 300 ml three-neck flask equipped with a stirring blade, a cooling pipe, and a nitrogen inlet tube and heated to 85° C. while flowing nitrogen. Thereafter, a solution obtained by mixing butyl methacrylate (manufactured by Wako Pure Chemical Industries, Ltd., 20 g), V-601 (trade name, manufactured by Wako Pure Chemical Industries, Ltd., 0.05 g), and ethanol (manufactured by Wako Pure Chemical Industries, Ltd., 17.5 g) was added dropwise into the system over 1.5 hours, and made to react while being stirred at 85° C. for 3 hours. Next, a solution containing an obtained polymer 1 (polymer compound (A)) was poured into a large amount of methanol, separated by filtration, and dried at 60° C. under reduced pressure. A cell adhesion test and a platelet adhesion test were performed using power of the obtained white solid (polymer 1 (37 g)). Further, when the molecular weight of the polymer 1 was measured, it was confirmed that the weight average molecular weight thereof was 15900.

(Cell Adhesion Test)

The polymer 1 was dissolved in hexafluoroisopropanol (manufactured by Wako Pure Chemical Industries, Ltd.) such that the mass ratio thereof was set to 1%, a glass substrate having a size of 24 mm$^2$ was coated with the obtained solution at 2000 rpm for 20 seconds using a spin coater, and then a glass substrate on which the coating film of the polymer 1 was formed was prepared.

Next, a glass substrate coated with the polymer 1 was put into a 6 well plate, mouse-derived fibroblasts (3T3 cells) were dispersed in Dulbecco's modified Eagle's medium such that the seeding density became $1.0 \times 10^4$ pieces/cm$^2$ and cultured at 37° C. for 24 hours under conditions of 5% carbon dioxide using an incubator.

Thereafter, the glass substrate was taken out and it was confirmed whether the cells adhered to the glass substrate using a phase contrast microscope (inverted cube research microscope, manufactured by Olympus Corporation). The magnification was set to 4 times.

Hereinafter, this operation was repeated ten times in total, and evaluation was performed based on the number (frequency) of glass substrates to which cells adhered as follows (test 101). In the test, at least "B" is acceptable.

A: 0 sheet
B: in a range of 1 to 3 sheets
C: 4 sheets or greater

In addition, as an example of an image of cells adhering to a glass substrate and an image of cells not adhering thereto, an image of a glass substrate is shown. Here, only a half of the glass substrate is coated with the polymer 1 (see FIG. 1: the right part is a coated portion and the left part is an uncoated portion).

(Platelet Adhesion Test)

The polymer 1 was dissolved in hexafluoroisopropanol (manufactured by Wako Pure Chemical Industries, Ltd.) such that the mass ratio thereof was set to 1%, and a CoCr piece having a size of 0.5×1 cm was immersed in the obtained solution, taken out, and then dried at 50° C. Next, the CoCr piece on which a coating film of the polymer 1 was formed was bonded to the tip of a polyethylene terephthalate (PET) strip having a size of 1×5 cm. Next, 0.5 to 1 cc of blood was sampled from an ether-anesthetized SPF mouse using a syringe, and the CoCr piece attached to the tip of PET was immersed in the obtained blood. Subsequently, the CoCr piece was washed with a phosphate buffer solution (manufactured by Wako Pure Chemical Industries, Ltd.) having a pH of 6.86 three times and immobilized with a 25% glutaraldehyde solution (manufactured by Wako Pure Chemical Industries, Ltd.) for 20 minutes. Thereafter, the CoCr piece was washed with distilled water, air-dried for 1 hour, and then coated with Au and Pd ions (MAGNETRON SPUTTER MSP-10, manufactured by Vacuum Device Inc.) for 3 minutes. The obtained CoCr piece was observed using a scanning electron microscope (manufactured by HITACHI high-technologies Co., Ltd.) and it was confirmed whether the platelets adhered to the CoCr piece. The magnification was set to 1000 times.

Hereinafter, this operation was repeated ten times in total, and evaluation was performed based on the number (frequency) of CoCr pieces to which platelets adhered as follows (test 101). In the test, at least "B" is acceptable.

A: 0 piece
B: in a range of 1 to 3 pieces
C: 4 pieces or greater

Evaluations of cell adhesion and platelet adhesion were performed in the same manners as described above except that the type and the weight ratio of the monomer constituting the polymer was changed (tests 102 to 104, c01, and c02). The results are listed in Table 1.

Example 2

(Preparation of Photocurable Composition)

The compound ex1 (4.5 g), 2-hydroxyethyl methacrylate (manufactured by Wako Pure Chemical Industries, Ltd., 4.5 g), triethylene glycol dimethacrylate (manufactured by Wako Pure Chemical Industries, Ltd., 0.8 g), IRGACURE 2959 (trade name, manufactured by BASF Corporation, 0.2 g), and methanol (3.3 g) were mixed with each other, thereby preparing a photocurable composition.

A glass substrate having a size of 24 mm$^2$ was coated with the obtained photocurable composition at 2000 rpm for 20 seconds using a spin coater, and then the coated surface of the glass substrate was irradiated with black light for 5 minutes, thereby preparing a glass substrate on which a photocurable coating film was formed.

A CoCr piece having a size of 0.5×1 cm was immersed in the obtained photocurable composition, taken out, and then irradiated with black light for 5 minutes, thereby preparing a CoCr piece on which a coating film of a photocured product was formed. The cell adhesion test and the platelet adhesion test were performed in the same manners as those in Example 1 and Reference Example 1, using the obtained glass substrate and the obtained CoCr substrate (test 201).

Reference Example 3

A CoCr substrate washed with acetone was washed with plasma and immersed in a 0.1 mass % methanol solution of 2-bromo-N-(3,4-dihydroxyphenethyl)propanamide synthesized according to J. Am. Chem. Soc., 205, 127, pp. 15843 to 15847 for 20 hours.

Next, the compound ex1 (7.2 g), water (24 g), methanol (19 g), 2-bromoisobutyrate (manufactured by Wako Pure Chemical Industries, Ltd., 0.016 g), and N,N,N',N'',N''-pentamethyldiethylene triamine (manufactured by Wako Pure Chemical Industries, Ltd., 0.346 g) were mixed with each other, and bubbled with nitrogen for 20 minutes while the mixture was stirred. Thereafter, the CoCr substrate was immersed in a mixed solution, copper bromide (I) was added thereto (manufactured by Wako Pure Chemical Industries, Ltd., 0.044 g), and then atom transfer radical polymerization (ATRP) was performed for 3 hours. Next, the obtained CoCr substrate was dried at 50° C., thereby obtaining a CoCr substrate on which a surface polymer graft film was formed. The cell adhesion test and the platelet adhesion test were performed in the same manners as those in Example 1 and Reference Example 1, using the obtained CoCr substrate (test 301).

From the results described above, according to the material non-adhesive to a biological substance of the present invention, it is understood that the adhesion of cells or blood components (platelets) can be suppressed or prevented. Therefore, it is understood that the material non-adhesive to a biological substance contributes to provision of not only artificial organs or medical instruments but also various sanitary products or members with improved biocompatibility, using the non-adhesive properties of the material to a biological substance.

Example 4 and Reference Example 4

A coating film of a polymer was formed using each of ex2, ex4, ex6, ex8, and ex9 in place of ex1 used in Reference Example 1. The cell adhesion test and the platelet adhesion test were performed in the same manners as those in Reference Example 1. As the result, it was confirmed excellent non-adhesive properties to a biological substance were shown in both tests (0 time, [A]).

TABLE 1

| No. | Betaine | BMA | HEMA | TEGDMA | Irg.2959 | Cell adhesion (n10) | Evaluation | Platelet adhesion (n10) | Evaluation |
|---|---|---|---|---|---|---|---|---|---|
| 101 | ex1 | 50 | 50 | | | 0 | A | 0 | A |
| 102 | ex10 | 50 | 50 | | | 0 | A | 0 | A |
| 103 | ex1 | 95 | 5 | | | 1 | B | 1 | B |
| 104 | ex1 | 4 | 96 | | | 1 | B | 2 | B |
| 201 | ex1 | 45 | | 45 | 8 | 2 | 0 | A | 0 | A |
| 301 | | ex1 or the like | | | | 0 | A | 0 | A |
| c01 | cex1 | 50 | 50 | | | 4 | C | 5 | C |
| c02 | cex3 | 50 | 50 | | | 4 | C | 4 | C |

Blending Amount: Parts by Mass

The compound and the blending amount thereof were listed together in a case of the betaine compound.

In regard to the number of the betaine compound, the above-described examples can be referred to.

In regard to the formulation in the test 301, the description above can be referred to.

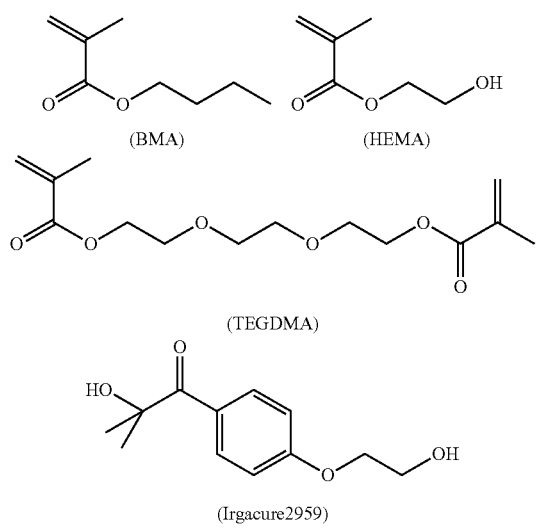

(BMA)  (HEMA)

(TEGDMA)

(Irgacure2959)

Reference Example 5

A polymer compound (copolymer) was synthesized by changing 5 parts of BMA from 50 parts thereof of the test 101 into the monomer of cex1. The same items of evaluations as in Table 1 were performed using the polymer compound and excellent performance was shown in both items of evaluations (0 time (A)).

Example 6

A photocurable composition was prepared by changing the photocurable composition of Example 2 as follows.

The compound ex1 (3 g), N-[tris(3-acrylamidepropoxymethyl)methyl]acrylamide (NTAA) (manufactured by Wako Pure Chemical Industries, Ltd., 6.7 g), IRGACURE 2959 (trade name, manufactured by BASF Corporation, 0.3 g), and methanol (40 g) were mixed with each other, thereby preparing a photocurable composition.

The cell adhesion test and the platelet adhesion test were performed in the same manners as those in Example 2 using the obtained photocurable composition (test 601). The results are listed in the following table.

TABLE 2

| No. | Betaine | NTAA | Irg.2959 | Cell adhesion (n10) | Evaluation | Platelet adhesion (n10) | Evaluation |
|---|---|---|---|---|---|---|---|
| 601 | ex1 | 30 | 67 | 3 | 0 | A | 0 | A |

From the results described above, it is understood that the excellent effects of the present invention are obtained in a case where a large amount of crosslinking agent is used.

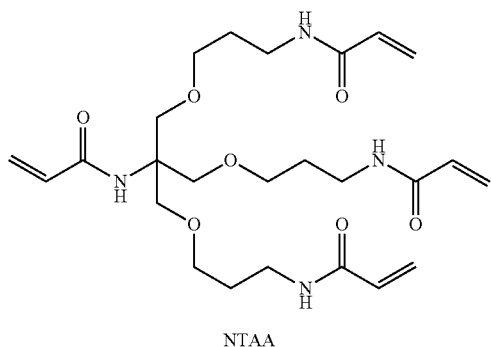

NTAA

The present invention has been described with reference to the embodiments, but the detailed description of the invention is not intended to limit the invention unless otherwise noted and the present invention should be broadly interpreted without departing from the spirit and the scope described in the aspects of the invention.

The present application claims priority based on Japanese Patent Application No. 2014-220307 filed in Japan on Oct. 29, 2014, Japanese Patent Application No. 2015-021539 filed in Japan on Feb. 5, 2015, and Japanese Patent Application No. 2015-149458 filed in Japan on Jul. 29, 2015 and the contents of which are incorporated herein by reference.

What is claimed is:

1. A material non-adhesive to a biological substance containing:
   a polymer compound (A) which includes a repeating unit derived from a sulfobetaine monomer represented by Formula (II), and which has a cross-linked structure,

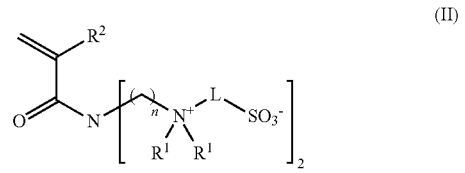

in the formulae, $R^1$ represents a methyl group, an ethyl group, an n-propyl group, or an isopropyl group, and a plurality of $R^1$'s may be the same as or different from each other, $R^2$ represents a hydrogen atom or a methyl group, n represents an integer of 2 to 4, and L represents a linear or branched alkylene group having 3 or 4 carbon atoms.

2. The material non-adhesive to a biological substance according to claim 1,
   wherein the monomer represented by Formula (II) is a monomer represented by the following Formula (II-1):

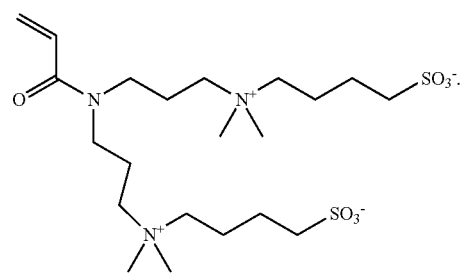

3. The material non-adhesive to a biological substance according to claim 1,
   wherein the polymer compound (A) includes a repeating unit derived from a copolymerizable monomer having an ethylenically unsaturated group, that can be copolymerized with the sulfobetaine monomer.

4. The material non-adhesive to a biological substance according to claim 1,
   wherein the content of the repeating unit derived from the sulfobetaine monomer in the polymer compound (A) is in a range of 5% to 90%, on a mass basis.

5. The material non-adhesive to a biological substance according to claim 1,
   wherein the biological substance is a cell or protein.

6. The material non-adhesive to a biological substance according to claim 1,
   wherein a C Log P value of the sulfobetaine monomer is −20 or greater and less than −7.2.

7. The material non-adhesive to a biological substance according to claim 1,
   wherein the cross-linked structure is a structure derived from at least one cross-linking agent selected from the following formulae (III) to (VII):

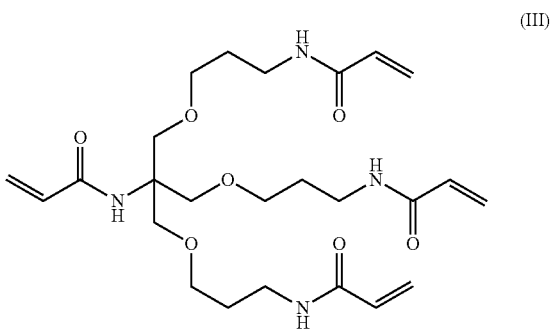

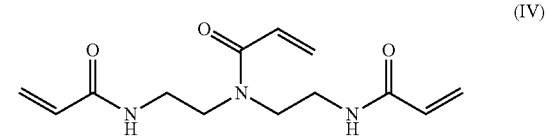

-continued
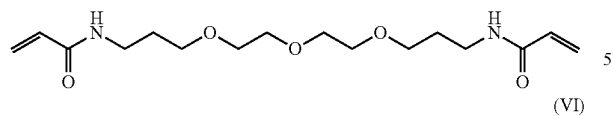
(V)
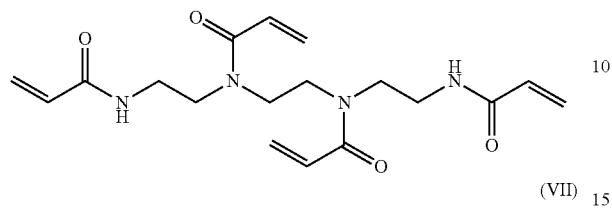
(VI)
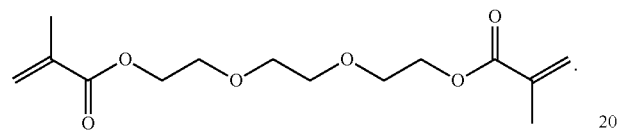
(VII)
8. An artificial organ comprising:
the material non-adhesive to a biological substance according to claim 1 in at least a portion thereof.
9. A medical instrument comprising:
the material non-adhesive to a biological substance according to claim 1 in at least a portion thereof.
* * * * *